United States Patent [19]

Zulliger et al.

[11] 3,963,922
[45] June 15, 1976

[54] X-RAY FLUORESCENCE DEVICE

[75] Inventors: Hans R. Zulliger; Lee M. Middleman, both of Portola Valley, Calif.

[73] Assignee: Nuclear Semiconductor, Menlo Park, Calif.

[22] Filed: June 9, 1975

[21] Appl. No.: 584,937

[52] U.S. Cl. .............................. 250/272; 250/273; 250/310; 250/311
[51] Int. Cl.² ...................... G21K 7/00; G21K 1/00; G01N 23/00; G01N 23/20
[58] Field of Search ............ 250/272, 310, 311, 273

[56] References Cited
UNITED STATES PATENTS

| | | | |
|---|---|---|---|
| 3,525,863 | 8/1970 | Constantine et al. | 250/273 |
| 3,567,928 | 3/1971 | Davies et al. | 250/310 |

OTHER PUBLICATIONS

Duncumb et al., "A Scanning Microscope for X-Ray Emission Pictures," X-Ray Microscopy and Microradiography, Proceedings of a Symposium Held at the Cavendish Laboratory, Cambridge, 1956, Academic Press, New York, 1957, pp. 374-380.

Primary Examiner—Alfred E. Smith
Assistant Examiner—T. N. Grigsby
Attorney, Agent, or Firm—Limbach, Limbach & Sutton

[57] ABSTRACT

An electron beam from an electron column instrument impinges on a target foil to produce a primary X-ray beam which, in turn, passes through a collimator to impinge on a specimen. The X-rays fluoresced from the specimen by the primary X-ray beam are detected by a solid state radiation detection device.

10 Claims, 11 Drawing Figures

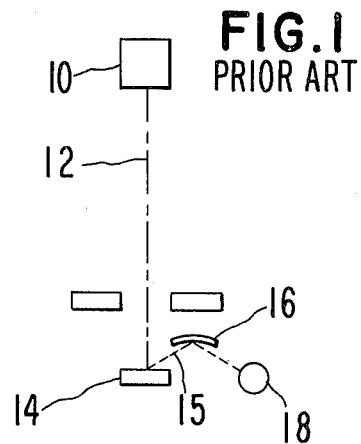
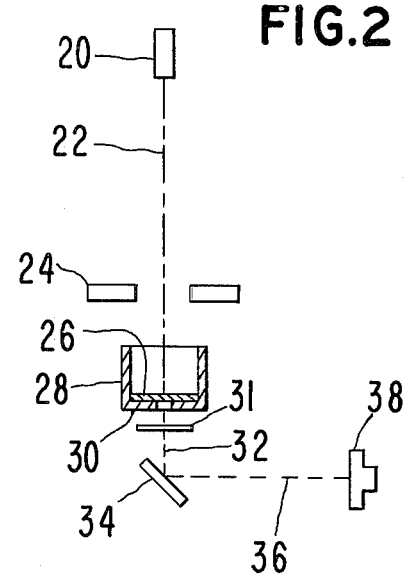
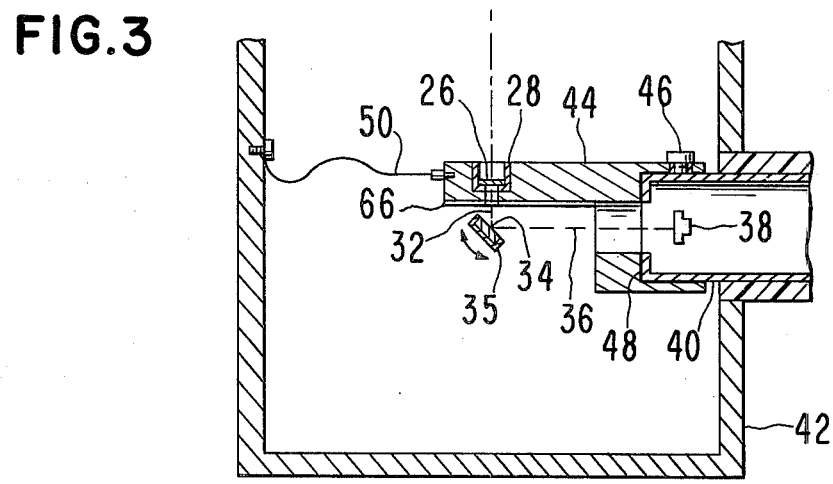
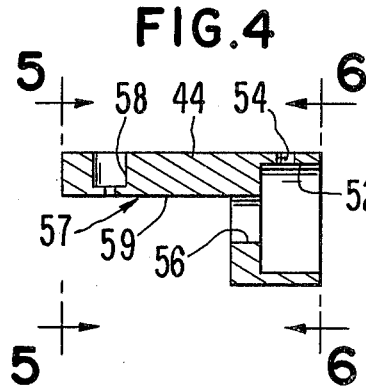
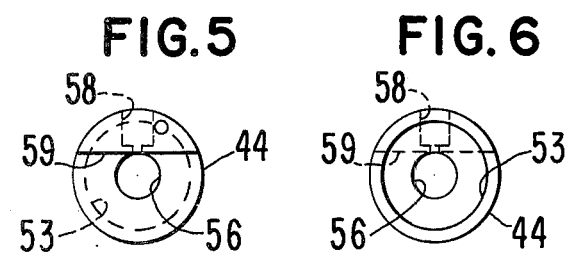

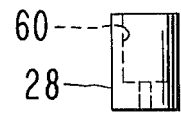
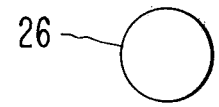
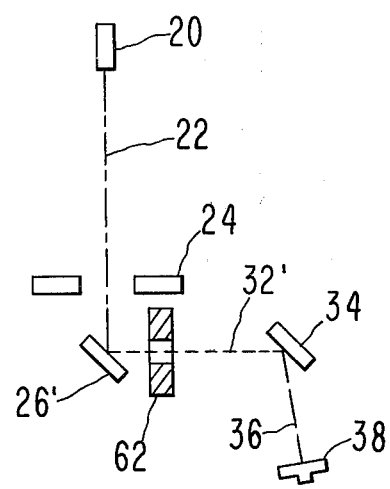
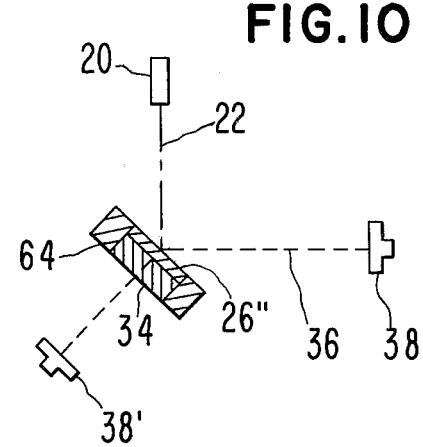
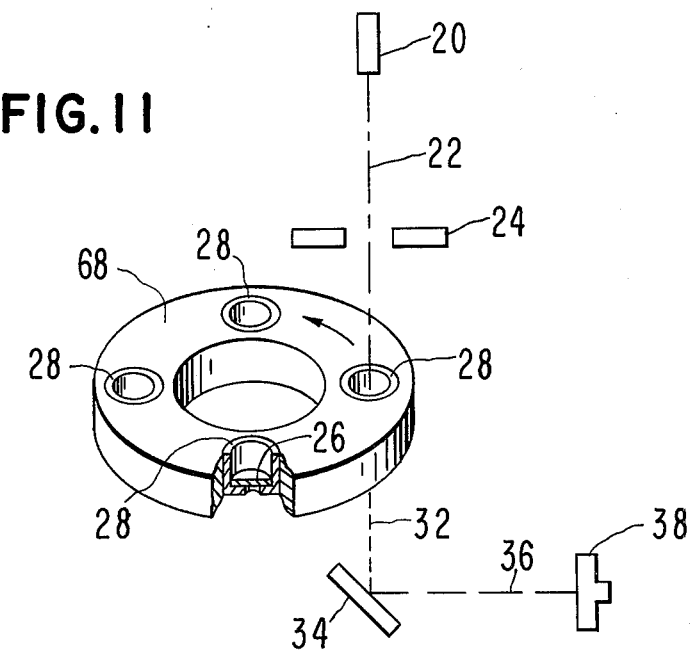

X-RAY FLUORESCENCE DEVICE

BACKGROUND OF THE INVENTION

The invention relates to X-ray fluorescence analysis and more particularly to X-ray fluorescence analysis in an electron column instrument.

X-ray fluorescence analysis in electron column instruments has become increasingly popular with the advent of highly efficient solid state radiation detection devices. In such devices the electron beam in the column instrument impinges directly on the specimen, producing Bremsstrahlung X-rays and fluorescent X-rays characteristic of the atomic elements in the sample material. Analysis of the fluorescence X-rays gives information about the sample. Since the electron range in most materials is typically on the order of a few microns, the X-ray fluorescence is restricted to the elements on the surface of the sample. Furthermore, the Bremsstrahlung X-rays are an undesirable background radiation which is superimposed upon the fluorescence X-ray spectrum, thus masking low concentrations of trace elements in the sample. This is known as the direct electron excitation method. A second method known as the X-ray excitation method uses an X-ray beam which impinges on a specimen placed outside of the sealed-off X-ray tube. The X-rays thereby fluoresced from the specimen are analyzed.

One problem with such X-ray tube type analysis is that the X-ray tubes are self-contained, and intrinsically lack the versatility of the electron column instrument. Also, there is a certain amount of X-ray absorption between the X-ray source and the specimen. Still another problem of the X-ray tube device is that the X-ray cannot be as easily manipulated as the electron beam in the electron column instrument. Still another problem with the X-ray tube device is that the sample stages are not easily accessible and precisely manipulatable.

SUMMARY OF THE INVENTION

The above and other problems are overcome by the present invention of a method and apparatus for converting an electron column instrument into an X-ray fluorescence analysis device by aiming the electron beam of the electron column instrument onto a target to thereby create a monochromatic X-ray beam which, in turn, impinges on a specimen to produce fluorescence X-rays which are analyzed by a detector.

In one preferred embodiment the target is interposed between the source of electrons and the specimen, while in a second embodiment the X-rays from the target are emitted back to a specimen which in turn produces the fluorescence X-rays which are analyzed.

The advantage of this method and apparatus is that the X-ray beam from the target penetrates into the bulk of the specimen, exciting atoms through the range of penetration. Therefore, the resultant fluorescence X-rays give information about the bulk of the specimen material rather than just its surface. The fact that the X-ray beam excites more of the sample and thus produces more fluorescence X-rays means that lower concentrations of elements can be detected in the same time interval. Furthermore, with the proper geometrical arrangement to be described hereinafter the amount of Bremsstrahlung X-rays reaching the detector can be reduced and therefore the signal-to-background noise ratio substantially improved. Although high spatial resolution is reduced by this technique, proper geometrical arrangements can, if desired, yield a certain degree of spatial resolution.

The conversion technique and apparatus described above use the same principles of excitation as conventional X-ray fluorescence analysis with X-ray tubes. The advantage of the described conversion technique and apparatus is that it incorporates all the sophisticated capabilities of an electron column instrument into the analysis system. X-ray tubes, which are self-contained, intrinsically lack the versatility of an electron column instrument. Some of the important capabilities available in many electron column instruments with the converted apparatus are:

1. The sample can be introduced into the same vacuum as the X-ray source, thus eliminating X-ray absorption between the source and the sample.
2. The electron beam can be manipulated by the excellent electron beam optics and scanning devices.
3. The specimen stages are easily accessible and precision manipulatable.
4. The X-ray detectors are either already in place or can be easily attached.
5. The conversion technique and apparatus of the present invention extend the usefulness of an electron column instrument, allowing it to operate either in the conventional mode giving high spatial resolution of surface characteristics of the specimen or in the converted mode to give sensitivity to small concentrations of elements in the bulk of the sample. The instrument is changed from one mode to the other by the simple insertion or removal of the conversion apparatus of the present invention.
6. The electron target can be readily changed, thus different primary X-ray beams can be produced.

Thus the method and apparatus of the present invention allows investigation of bulk material effects, macro-X-ray fluorescence analysis, and improved fluorescence efficiency for "high" Z elements, i.e., those elements whose absorption edge lies just below the electron column operating voltage. None of these features are possible with existing electron column techniques.

It is therefore an object of the present invention to provide an X-ray fluorescence device in which the specimen can be introduced into the same vacuum as the X-ray source, thus eliminating X-ray absorption between the source and the specimen. The beam and the specimen stage can be readily manipulated, and the stage is easily accessible.

It is another object of the invention to provide apparatus for converting a conventional electron column instrument into an X-ray fluorescence device.

It is still another object of the invention to provide an X-ray fluorescence device which allows analysis of small concentrations of elements in the bulk sample specimen.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagrammatic illustration of the prior art X-ray fluorescence analysis devices;

FIG. 2 is a diagrammatic illustration of one embodiment of the invention;

FIG. 3 is a vertical view, in section, with portions broken away, of the embodiment of the invention schematically illustrated in FIG. 2;

FIG. 4 is a vertical view, in section, of the frame for the embodiment depicted in FIG. 3;

FIG. 5 is an end view of the frame taken generally along the lines 5—5 of FIG. 4;

FIG. 6 is an end view of the frame taken generally along the lines 6—6 of FIG. 4;

FIG. 7 is an enlarged view of the collimator for the embodiment depicted in FIG. 3;

FIG. 8 is an enlarged view of the target foil for use in the embodiment depicted in FIG. 3;

FIG. 9 is a diagrammatic view of a second embodiment of the invention;

FIG. 10 is a diagrammatic view of a third embodiment of the invention; and

FIG. 11 is a diagrammatic view of a modification of the embodiment depicted in FIG. 2.

DETAILED DESCRIPTION OF CERTAIN PREFERRED EMBODIMENTS

Referring now more particularly to FIG. 1 various types of conventional X-ray fluorescence analysis devices are diagrammatically illustrated. In such systems a source of rays can generate either X-rays or β-rays, such as in U.S. Pat. No. 2,928,944, or electrons, such as is described in U.S. Pat. No. 3,155,827. These rays 12, of whatever nature, impinge directly upon a specimen 14 to fluoresce X-rays 15. The fluoresced X-rays 15 strike a crystal reflector 16 and are redirected to an X-ray detector 18. The various problems with such apparatus have been described in detail above. When a radiation source such as an X-ray tube is used for the source 10, the specimen 14 lies outside the vacuum chamber containing the source 10 and some of the X-rays are absorbed by the X-ray tube window (not shown). When an electron gun is used as the source 10, Bremsstrahlung X-rays are produced at right angles to the electron beam. The Bremsstrahlung X-rays are not produced by the target, per se, but are simply the result of the slowing down of the electrons. These Bremsstrahlung rays interfere with the detection of the fluoresced X-rays.

Referring now more particularly to FIG. 2, one preferred embodiment of the invention is diagrammatically illustrated. In this embodiment an electron beam source 20 generates a beam of electrons 22 which are focused by an electromagnetic lens 24 to strike a metallic target foil 26 situated within the recess of a hollow metallic collimator 28. The recess within the collimator is provided with a restricted diameter portion 30 on the side of the foil 26 opposite to the source of electrons 20. The electron beam 22 striking the foil 26 fluoresces X-rays which are collimated by the collimator 28 into a primary, monochromatic X-ray beam 32 which passes through the restricted portion 30 of the collimator 28. The fluoresced X-ray beam 32 is directed to strike a specimen 34 mounted directly in line with the source of electrons 20 and with the foil 26 interposed between the two. The X-ray beam 32 striking the specimen 34 fluoresces X-rays 36 which are directed to strike a solid state X-ray detector 38. A filter 31 may be placed between the target foil 26 and the specimen 34 to further insure that the beam 32 is monochromatic.

One advantage of the embodiment depicted in FIG. 2 is that the Bremsstrahlung rays produced when the electron beam 22 strikes the foil 26 are absorbed by the collimator 28 and do not interfere with the detection of the fluoresced X-rays from the specimen 34. Bremsstrahlung radiation is emitted primarily in the directions perpendicular to the electron beam 22 when the electron beam 22 strikes the foil 26.

Referring now more particularly to FIG. 3 the embodiment depicted diagrammatically in FIG. 2 is illustrated in greater detail. As mentioned above, the apparatus of the invention is adapted for use in any type of electron column instrument and the details of such an instrument are well known in the art and therefore are not depicted in detail in the Figures.

In order to provide a target for the production of the primary X-ray beam 32, a device is attached to an energy-dispersive X-ray spectrometer (EDS) cap 40 which is mounted in the wall 42 of the target chamber of an electron column instrument. This device comprises the X-ray target foil 26, which can be readily changed, which is mounted in the X-ray shield and collimator 28 which serves the purpose of confining and directing the primary X-rays. The collimator 28 is mounted in a frame 44 which is mounted concentrically over the end of the end cap 40 within the vacuum chamber 42 and is held in place by a set screw 46 which is insulated from the end cap 40. Because the frame 44 is attached to the end cap 40 it may be moved into the electron beam 22 and retracted out of it remotely. When retracted, both the electron column instrument and the end cap can be used in their conventional manner. A simpler device could be affixed to the electron pole piece, in other embodiments, but it would not be as conveniently removable. In still other embodiments the frame 44 could be attached to the sample stage or any other structural part of the electron column instrument.

The frame 44 is isolated from the end cap 40 by means of an electrical insulator layer 48 interposed between the frame 44 and the end cap 40. The insulator 48 may be, for example, a 10 mil thick self-adhesive Teflon layer. This insulation layer 48 reduces electrical signal noise generated by electrical ground loops and prevents the discharging through the end cap 40 of an electrical charge built up in the frame 44 due to the electron beam 22. A grounding wire 50 is connected between the frame 44 and the target chamber wall 42 to prevent this electric charge build-up in the frame 44.

The X-ray target foil is preferably a high purity elemental foil such as molybdenum, copper, tungsten, silver, or the like. The foil thickness is chosen to provide absorption of the electron beam, maximum X-ray flux, minimum X-ray background and preferential excitation of the specimen elements. The foil is positioned in the collimator 28 to direct the primary X-ray beam onto the specimen 34. Because the detector 38 is at an angle to the X-ray beam 32 the primary X-rays cannot strike the detector 38. The distance between the foil and the specimen 34 and between the foil and the electron column pole piece 24 are adjustable to vary the amount of the specimen exposed to the primary X-ray beam, the X-ray background and the detector solid angle. Also, the specimen is mounted on a tiltable table 35 to allow for adjustment of the angle of incidence of the primary X-ray beam 32 upon the specimen.

Referring now more particularly to FIGS. 4, 5 and 6, the frame 44 is machined from a metal cylinder. At one end of the cylinder an axial bore 52 is made to receive the end of the end cap 40 as shown in FIG. 3. A diametric hole 54 is bored in this same end to intersect the bore 52 to accommodate the set screw 46. The bore 52 is reduced in diameter to provide a smaller bore 56 through which the X-ray beam 36 will pass to strike the detector 38.

The metallic cylinder is cut along a cord which is tangent to the periphery of the bore 56. The larger portion of the cylinder divided by the cord is removed and the remaining portion 57 is radially bored at one end to form a hole 58 to receive the collimator 28. The bore 58 may have a diameter of, for example, 200 mils and is reduced in diameter to approximately 50 mils at its exit point at the flat surface 59 of the portion 57 defined by the chord. The thickness of the reduced diameter portion taken along the direction of the electron beam is approximately 30 mils. This thickness shields the specimen from any X-rays produced in the collimator 28. It should be apparent that these distances are for illustrative purposes only. The frame 44 is constructed of aluminum in the preferred embodiment, although in other embodiments it may be constructed of other suitable materials. The flat surface 59 is thereafter coated with an X-ray absorbing layer of carbon 66 (FIG. 3).

Referring now more particularly to FIG. 7 the collimator 28 is basically a cylindrical member having a longitudinal bore 60 which is reduced in diameter at the exit point adjacent the specimen 34. The collimator 28 is fabricated from tungsten in the preferred embodiment and is adapted to push fit into the bore 58 in the frame 44. The target foil 26 is basically a flat disc which is dimensioned to have a loose fit within the bore 60 in the collimator 28 (see FIG. 8).

The portion of the frame 44 surrounding the bore 56 acts as a collimator for the X-ray detector 38 and reduces the amount of Bremsstrahlung X-rays which can enter the end cap 40. This collimator also restricts the view of the end cap 40 to the specimen 34 under examination.

The primary X-ray beam 32 impinges on the specimen 34 and penetrates its surface. The fluorescent X-rays 36 which are characteristic of the constituent elements of the sample are produced at the surface and also within the bulk of the material. A portion of these fluorescence X-rays are then viewed by the detector 38.

The primary X-rays 32 can penetrate much deeper into the specimen than the electrons which produce the primary X-rays in the target foil. Thus, depending upon the energy of the electron beam, the target foil used, and the specimen composition, fluorescence X-rays are produced deep within the specimen and can be measured. This fact permits the detection of lower elemental concentrations and bulk sample analysis rather than just elemental surface analysis.

Because the electron beam, the X-ray target, and the specimen are all in the same vacuum chamber, better X-ray optics are possible than with conventional X-ray tubes. Also no vacuum windows are present between the X-ray target and the specimen. This reduces absorption and scattering problems.

If an extremely thin or perforated X-ray target foil 26 is used, some electrons from the beam 22 will pass through the foil and will impinge upon the specimen 34 to provide some spatial resolution by viewing the back scattered or secondary electrons, as with conventional electron column operation.

While the embodiment described in reference to FIGS. 2 and 3 is the preferred embodiment there are other, less advantageous embodiments of the invention. Referring now more particularly to FIG. 9, in a second embodiment of the invention the electron beam 22 is caused to strike a target 26' corresponding to the target foil 26 in the embodiment described above, to produce a primary X-ray beam 32' which is directed through a collimator 62 to impinge upon the specimen 34. The X-ray beam 36 fluoresced from the specimen 34 is directed to strike the detector 38 as in the above described embodiment. One major difference between the embodiment depicted in FIG. 9 and that depicted in FIGS. 2 and 3 is that the primary X-ray beam 32' is "reflected" to the specimen 34 rather than emanating from the opposite side of the target 26' as in the embodiment depicted in FIGS. 2 and 3. Thus this embodiment is far less advantageous than the embodiment depicted in FIGS. 2 and 3 because it is less effective in masking the Bremsstrahlung X-rays. The purpose of the collimator 62 is to absorb as much of the Bremsstrahlung X-rays as is possible while still allowing the primary X-ray beam 32' to strike the specimen 34. The frame structure depicted in FIG. 3 may be appropriately adapted to accommodate the embodiment depicted in FIG. 9 so that the advantages of converting an electron column instrument are still obtained.

Referring now more particularly to FIG. 10, still another embodiment of the invention is depicted in which the target foil 26'' is evaporated directly onto the specimen 34. The X-ray beam 36 which is fluoresced from the specimen 34 is again directed to strike the detector 38. Two positions for the detector 38 are shown. The transmission position 38' could be used for thin targets. The target foil 26'' and the sample 34 would then be somewhat effective in stopping Bremsstrahlung X-rays, although less effective than the embodiment depicted in FIGS. 2 and 3. The specimen 34 can be suitably mounted in a holder 64 which also acts to absorb some of the Bremsstrahlung X-rays. The embodiment of FIG. 10 is, however, suitable for use in converting an electron column instrument and thus has the advantages described above with respect to the preferred embodiment.

Although the above embodiments have been described as having a single foil 26, in other embodiments, as best illustrated in FIG. 11, it is possible to provide for multiple target foils 26 mounted in a rotary tray 68 which is remotely rotated to place the desired target foil in line with the electron beam 22. In still other embodiments, a second filter foil can be placed below the target foil to reduce the Bremsstrahlung X-rays and the general X-ray background.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

What is claimed is:

1. Apparatus for adapting an electron column instrument for X-ray fluorescence analysis of a sample, the electron column instrument being of the type having means for generating an electron beam and a surrounding evacuated chamber, the adapting apparatus comprising:

a target foil positioned to be struck on one side by the electron beam to thereby produce a fluorescent, primary X-ray beam directed to impinge upon the sample, energy dispersive X-ray spectrometer means for detecting X-rays fluoresced from the sample by the primary X-ray beam, and wherein the target foil, sample, and detecting means are contained within the evacuated chamber.

2. Apparatus as recited in claim 1 wherein the target foil is oriented with respect to the electron beam such that the primary X-ray beam fluoresced from the target foil emanates from a side opposite to the one side struck by the electron beam.

3. Apparatus as recited in claim 2 further comprising means for collimating the primary X-ray beam and wherein the target foil is disposed within the collimating means.

4. Apparatus as recited in claim 3 wherein the collimating means comprises a hollow cylinder whose longitudinal axis is aligned with the beam of electrons, the target foil being positioned within the hollow cylinder and the interior of the cylinder being reduced in diameter on the side of the target foil opposite to the one side.

5. Apparatus as recited in claim 4 wherein the hollow cylinder is made of a material which is X-ray absorbing.

6. Apparatus as recited in claim 1 wherein the target foil is deposited directly on the sample.

7. Apparatus as recited in claim 1 further comprising multiple target foils and means for positioning selected ones of the target foils to be struck by the electron beam.

8. Apparatus as recited in claim 1 wherein the target foil is sufficiently thin that a portion of the electron beam passes through the target foil to strike the sample.

9. Apparatus as recited in claim 1 wherein the target foil is perforated to allow a portion of the electron beam to pass through the target foil and strike the sample.

10. Apparatus for X-ray fluorescence analysis of a sample comprising electron column instrument means for generating an electron beam, a target positioned to be struck by the electron beam to thereby produce a primary fluorescent X-ray beam directed to impinge upon the sample, and wherein the target is struck on one side by the electron beam and the primary X-ray beam exits from the same side of the target as is struck by the electron beam, energy dispersive X-ray spectrometer means for detecting X-rays fluoresced from the sample by the primary X-ray beam, and an evacuated chamber surrounding the electron column instrument means, the target, the sample and the detecting means.

* * * * *